United States Patent
Hirao et al.

(10) Patent No.: US 7,886,604 B2
(45) Date of Patent: Feb. 15, 2011

(54) ELECTROMAGNETIC ULTRASONIC FLAW DETECTION METHOD AND ELECTROMAGNETIC ULTRASONIC TRANSDUCER TO BE USED THEREFOR

(75) Inventors: Masahiro Hirao, Osaka (JP); Hirotsugu Ogi, Osaka (JP); Tsutomu Kikuchi, Ichihara (JP); Kiyohazu Fujimaki, Osaka (JP)

(73) Assignees: Idemitsu Kosan Co., Ltd., Tokyo (JP); Japan Industrial Testing Corporation, Osaka (JP)

( * ) Notice: Subject to any disclaimer, the term of this patent is extended or adjusted under 35 U.S.C. 154(b) by 554 days.

(21) Appl. No.: 11/960,091

(22) Filed: Dec. 19, 2007

(65) Prior Publication Data

US 2008/0178679 A1   Jul. 31, 2008

Related U.S. Application Data

(60) Provisional application No. 60/897,494, filed on Jan. 26, 2007.

(51) Int. Cl.
*G01N 29/265* (2006.01)
*G01N 29/12* (2006.01)

(52) U.S. Cl. .......................................... 73/643; 73/623
(58) Field of Classification Search .................... 73/623, 73/643, 622, 579
See application file for complete search history.

(56) References Cited

U.S. PATENT DOCUMENTS

| | | | | |
|---|---|---|---|---|
| 3,916,699 A | * | 11/1975 | Moran et al. | 73/623 |
| 4,320,661 A | * | 3/1982 | Peterson et al. | 73/643 |
| 4,471,658 A | * | 9/1984 | Morimoto | 73/643 |
| 4,665,752 A | * | 5/1987 | Huschelrath et al. | 73/643 |
| 5,164,921 A | * | 11/1992 | Graff et al. | 367/140 |

(Continued)

FOREIGN PATENT DOCUMENTS

JP    2001-50936 A    2/2001

(Continued)

OTHER PUBLICATIONS

T. Kikuchi; "Improvements of reliability of installation and efforts on engineering works"; The 37th meeting for research and debate on equipment; Institute of Petroleum, Dec. 20, 2006.

*Primary Examiner*—Hezron Williams
*Assistant Examiner*—Rose M Miller
(74) *Attorney, Agent, or Firm*—Westerman, Hattori, Daniels & Adrian, LLP (57) ABSTRACT

An electromagnetic ultrasonic flaw detection method is provided which ensures highly accurate inspection of an interior surface of a fin-implanted heat transfer tube for detection of corrosion and requires less time for the inspection, no contact medium such as water, and less time and less costs for a pretreatment. The method may include moving an EMAT in a fin-implanted heat transfer tube of an air cooling heat exchanger axially of the tube; causing the EMAT to generate an axially symmetric SH wave by utilizing an electromagnetic force to vibrate a tube body of the fin-implanted heat transfer tube to cause resonance; causing the EMAT to detect a resonant frequency; and if the detected resonant frequency is different from a resonant frequency observed when the tube body has a normal wall thickness, judging that an interior surface of the tube body has a corroded portion.

8 Claims, 7 Drawing Sheets

U.S. PATENT DOCUMENTS

| | | | |
|---|---|---|---|
| 5,808,202 A * | 9/1998 | Passarelli, Jr. | 73/643 |
| 5,907,100 A * | 5/1999 | Cook | 73/602 |
| 6,896,171 B2 * | 5/2005 | Den Boer et al. | 228/103 |
| RE40,515 E * | 9/2008 | Kwun et al. | 324/220 |

FOREIGN PATENT DOCUMENTS

| | | |
|---|---|---|
| JP | 2002-296241 A | 10/2002 |
| JP | 2004-301613 A | 10/2004 |

* cited by examiner

ELECTROMAGNETIC ULTRASONIC FLAW DETECTION METHOD AND ELECTROMAGNETIC ULTRASONIC TRANSDUCER TO BE USED THEREFOR

RELATED APPLICATIONS

This application claims the benefit of U.S. Provisional Application No. 60/897,494, filed Jan. 26, 2007.

BACKGROUND OF THE INVENTION

1. Field of the Invention

The present invention relates to an electromagnetic ultrasonic flaw detection method for inspecting a fin-implanted heat transfer tube of an air cooling heat exchanger for detection of corrosion, and an electromagnetic ultrasonic transducer to be used for the method.

2. Description of the Related Art

If an interior surface of a finned heat transfer tube of an air cooling heat exchanger is corroded to a greater extent, a fluid flowing through the tube is liable to leak out of the tube. Therefore, the interior surface of the finned heat transfer tube is inspected for detection of corrosion.

Examples of a conventional inspection method for detecting the corrosion of the interior surface of the finned heat transfer tube include an eddy current flaw detection method which utilizes an AC magnetic flux generated by a coil provided in a probe for flaw detection (see, for example, Japanese Unexamined Patent Publication No. JP-A1-2002-296241), and an ultrasonic flaw detection method which utilizes ultrasonic waves generated by oscillating an oscillator for flaw detection (see, for example, Japanese Unexamined Patent Publication No. JP-A1-2001-50936).

Where the tube has fins, however, the eddy current flaw detection method fails to detect the corrosion of the interior surface of the tube with high accuracy due to obstruction by the fins. This makes it impossible to employ the eddy current flaw detection method for the detection of the corrosion of the interior surface of the finned heat transfer tube. On the other hand, the ultrasonic flaw detection method requires greater time for inspection of a single heat transfer tube, making it impossible to perform 100% inspection in a short period of time because of its lower inspection speed. In addition, the heat transfer tube should be filled with water for the inspection, so that a post treatment such as dehydration should be performed. In some cases, the water cannot be used depending on the type of the fluid passing through the heat transfer tube. Further, the interior surface of the heat transfer tube should be scaled for increasing the inspection accuracy. Therefore, time and costs are required for the scaling and other pretreatments.

In view of the foregoing, it is an object of the present invention to provide an electromagnetic ultrasonic flaw detection method which ensures highly accurate inspection of an interior surface of a fin-implanted heat transfer tube for detection of corrosion, and requires less time for the inspection, no contact medium such as water, and less time and less costs for a pretreatment, and to provide an electromagnetic ultrasonic transducer to be used for the method.

SUMMARY OF THE INVENTION

According to a first aspect of the present invention to achieve the aforementioned object, there is provided an electromagnetic ultrasonic flaw detection method, which comprises: moving an electromagnetic ultrasonic transducer in a fin-implanted heat transfer tube of an air cooling heat exchanger axially of the tube; causing the electromagnetic ultrasonic transducer to generate an axially symmetric SH wave by utilizing an electromagnetic force to vibrate a tube body of the fin-implanted heat transfer tube to cause resonance; causing the electromagnetic ultrasonic transducer to detect a resonant frequency; and, if the detected resonant frequency is different from a resonant frequency observed when the tube body has a normal wall thickness, judging that an interior surface of the tube body has a corroded portion.

According to a second aspect of the present invention, there is provided an electromagnetic ultrasonic transducer which comprises: a permanent magnet unit having a hollow or solid cylindrical shape; and a transmission coil and a reception coil which are wound around the permanent magnet unit; wherein the permanent magnet unit includes a plurality of permanent magnets each having opposite poles respectively disposed at a greater radius portion and a smaller radius portion thereof, and arranged circularly with their polarities alternately reversed circumferentially of the permanent magnet unit; wherein the permanent magnet unit has opposite end faces each formed with a plurality of slits intersecting each other.

Inventors of the present invention have conducted intensive studies on a flaw detection method which ensures highly accurate inspection of an interior surface of a finned heat transfer tube of an air cooling heat exchanger for detection of corrosion. As a result, the inventors have found that, where the finned heat transfer tube is a fin-implanted heat transfer tube, the use of an electromagnetic ultrasonic transducer (hereinafter referred to as "EMAT") ensures highly accurate detection of a resonant frequency which is achieved by moving the EMAT in the fin-implanted heat transfer tube axially of the tube, causing the EMAT to generate an axially symmetric SH wave by utilizing an electromagnetic force to vibrate a tube body of the fin-implanted heat transfer tube to cause resonance, and causing the EMAT to detect the resonant frequency. Further, the inventors have found that the corrosion of the interior surface of the heat transfer tube can be highly accurately detected by comparing the detected resonant frequency with a resonant frequency observed when the tube body has a normal wall thickness and, if the detected resonant frequency is different from the normal resonant frequency, judging that the interior surface of the tube body has a corroded portion, and have attained the present invention. In addition, the use of the EMAT makes it possible to achieve the flaw detection in a shorter period of time than the conventional ultrasonic flaw detection method, thereby permitting 100% inspection within a process at reduced costs. Further, the EMAT does not require a contact medium such as water, obviating the need for the post treatment (dehydration or the like) of the tube body. The inspection for the flaw detection can be performed on any heat transfer tube irrespective of the type of a fluid passing through the heat transfer tube. Since the EMAT is adapted for non-contact inspection, the tube body can be inspected for corrosion even with scale deposited on the interior surface of the tube body. Therefore, time and costs required for a pretreatment can be reduced. In the present invention, the finned heat transfer tube is limited to the fin-implanted heat transfer tube. This is because, where the finned heat transfer tube is of a type which has an outer layer formed integrally with fins on the entire outer periphery or a part of the outer periphery of the tube body of the finned heat transfer tube (e.g., a heat transfer tube having L-shaped wound fins), the resonant frequency does not occur in a portion of the tube body formed with the outer layer due to the influence of the outer layer.

The inventive EMAT includes a permanent magnet unit having a hollow or solid cylindrical shape, and a transmission coil and a reception coil which are wound around the permanent magnet unit. The permanent magnet unit includes a plurality of permanent magnets each having opposite poles respectively disposed at a greater radius portion and a smaller radius portion thereof, and arranged circularly with their polarities alternately reversed circumferentially of the permanent magnet unit. Therefore, when a high frequency electric current flows through the transmission coil, the axially symmetric SH wave is generated in the tube body of the fin-implanted heat transfer tube to vibrate the tube body to cause resonance in the tube body, and a resonant frequency is detected by the reception coil of the EMAT. Therefore, the inventive EMAT can be used as the EMAT for the inventive electromagnetic ultrasonic flaw detection method. In addition, the permanent magnet unit has opposite end faces (axially opposite end faces) each formed with a plurality of slits intersecting each other. The slits improve the S/N ratio (signal-to-noise ratio), thereby reducing the noise. In this case, the permanent magnet unit preferably has annular slits provided in opposite end portions (axially opposite end portions) of an outer peripheral surface thereof as extending circumferentially thereof for further improvement of the S/N ratio. The slits are preferably recessed grooves (each having a flat bottom shape). Where the slits are provided in the opposite end faces and where the slits are provided in the opposite end portions of the outer peripheral surface and in the opposite end faces, the number of the slits provided for each direction may be one, or two or more. In the present invention, the expression "intersecting each other" means that the slits intersect each other at oblique angles or that the slits perpendicularly intersect each other. The slits perpendicularly intersecting each other further improves the S/N ratio.

In the inventive electromagnetic ultrasonic flaw detection method, the tube body of the fin-implanted heat transfer tube is composed of a carbon steel (a ferromagnetic material) and fins of the heat transfer tube are composed of a nonferrous material such as aluminum. The inventive electromagnetic ultrasonic flaw detection method can be employed for a common fin-implanted heat transfer tube.

In the inventive electromagnetic ultrasonic flaw detection method, the resonant order of the axially symmetric SH wave is the first order mode which is the lowest resonant order mode. The method is suitable for inspecting the interior surface of the fin-implanted tube for detection of corrosion, and ensures highly accurate inspection.

In the inventive electromagnetic ultrasonic flaw detection method, the EMAT includes a permanent magnet unit having a hollow or solid cylindrical shape, and a transmission coil and a reception coil which are wound around the permanent magnet unit, wherein the permanent magnet unit includes a plurality of permanent magnets each having opposite poles respectively disposed at a greater radius portion and a smaller radius portion thereof and arranged circularly with their polarities alternately reversed circumferentially of the permanent magnet unit. The corrosion of the interior surface of the fin-implanted heat transfer tube can be highly accurately detected by employing the inventive EMAT as the EMAT for the inventive electromagnetic ultrasonic flaw detection method.

DETAILED DESCRIPTION OF THE PREFERRED EMBODIMENTS

Next, embodiments of the present invention will be described in detail on the basis of the attached drawings.

Figure 1:
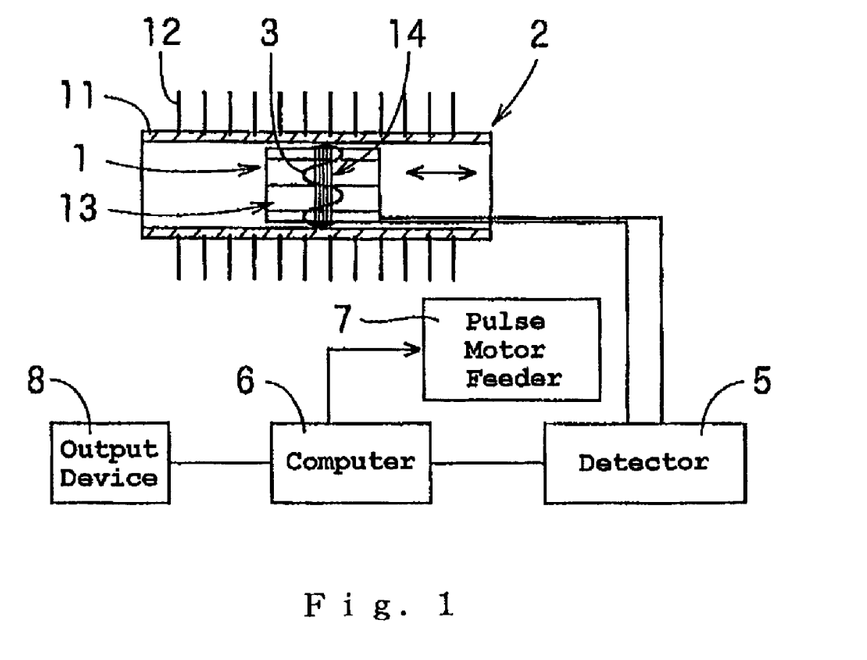
FIG. 1 is an explanatory diagram illustrating an electromagnetic ultrasonic flaw detection apparatus to be employed for an electromagnetic ultrasonic flaw detection method according to one embodiment of the present invention.

FIG. 1 illustrates an electromagnetic ultrasonic flaw detection apparatus to be employed for an electromagnetic ultrasonic flaw detection method according to one embodiment of the present invention. In this figure, a reference numeral 1 denotes a generally hollow cylindrical EMAT which is inserted in a fin-implanted heat transfer tube (fin-implanted tube) 2 and moved axially of the tube to inspect an interior surface of the fin-implanted heat transfer tube 2 for flaw detection by utilizing axially symmetric SH waves 3 generated by an electromagnetic force by the EMAT 1 (and propagating circumferentially of the tube). A reference numeral 5 denotes a detector including an amplifier, a burst wave generator, an A/D converter and the like, and a reference numeral 6 denotes a computer for analyzing an input signal. A reference numeral 7 denotes a pulse motor feeder for inserting the EMAT 1 into the fin-implanted heat transfer tube 2 and moving the EMAT 1 axially of the tube, and a reference numeral 8 denotes an output device.

Figure 2:
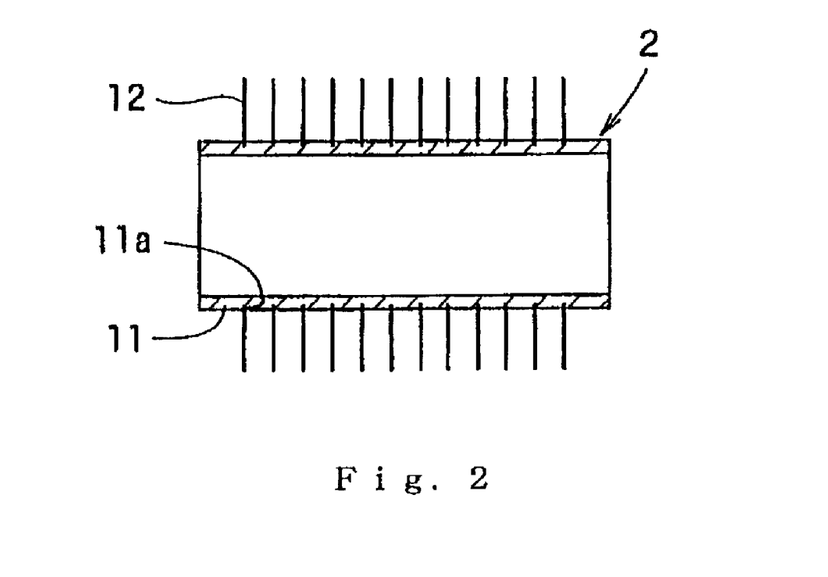
FIG. 2 is a diagram for explaining the construction of a fin-implanted heat transfer tube.

The fin-implanted heat transfer tube 2 is employed for an air cooling heat exchanger, and includes a hollow cylindrical tube body 11 of a carbon steel and heat transfer fins 12 of a nonferrous metal such as aluminum arranged helically on an outer periphery of the tube body 11 as projecting from the outer periphery (with inner edge portions of the heat transfer fins 12 implanted in a helical groove 11a formed in the outer periphery of the tube body 11) (see FIG. 2).

Figure 3:
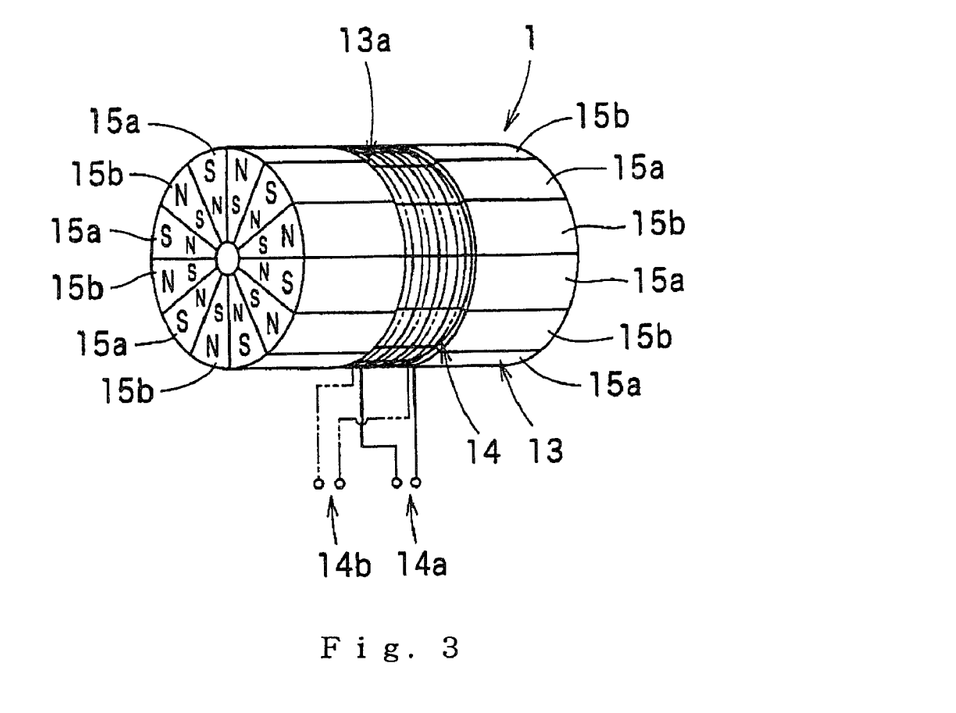
FIG. 3 is a perspective view illustrating an EMAT.
Figure 4:
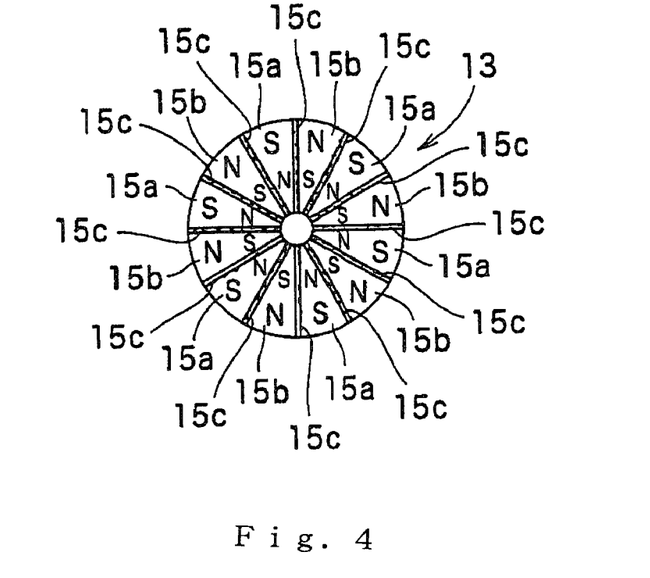
FIG. 4 is a diagram for explaining the EMAT.

As shown in FIG. 3, the EMAT 1 includes a generally hollow cylindrical magnet unit 13, and a pair of spiral coils 14 (a transmission spiral coil 14a and a reception spiral coil 14b) wound around an annular recess 13a of the magnet unit 13. The magnet unit 13 includes a plurality of permanent magnets 15a, 15b each having opposite poles respectively disposed at a greater radius portion and a smaller radius portion thereof and arranged circularly with their polarities alternately reversed circumferentially of the magnet unit, and serves as a circular magnet arrangement for generating alternating magnetic fields. The permanent magnets 15a, 15b each have a bar shape. The permanent magnets are configured in the same shape except for their polarities. With the permanent magnets combined into the magnet unit 13, the magnet unit 13 is circumferentially equiangularly segmented. Adjacent ones of the permanent magnets 15a, 15b are bonded and fixed to each other with an adhesive layer 15c of an epoxy resin (not shown in FIG. 3, but see FIG. 4). The adhesive layer 15c suppresses the influence (runaway) of the magnetic flux of the permanent magnet 15a (15b) on the adjacent permanent magnet 15b (15a).

Figure 5:
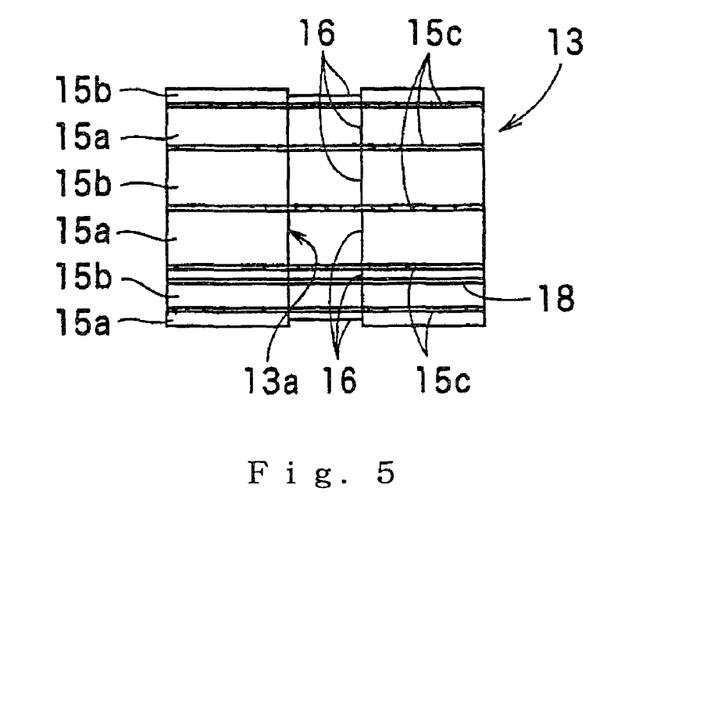
FIG. 5 is a side view of a magnet unit.
Figure 7:
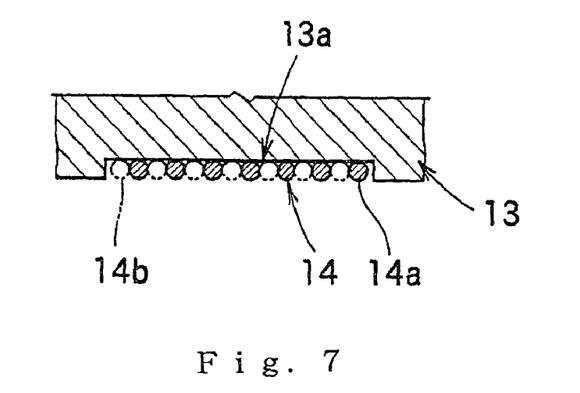
FIG. 7 is a diagram for explaining a spiral coil.

The magnet unit 13 will be described in greater detail. The circular magnet arrangement for generating alternating magnetic fields is produced by alternately arranging permanent magnets 15a each having an S-pole at a greater radius portion thereof and permanent magnets 15b each having an N-pole at a greater radius portion thereof and bonding and fixing adjacent ones of the permanent magnets 15a and 15b to each other, and adapted to generate alternating magnetic fields with the polarities alternately reversed circumferentially of the permanent magnet unit (see FIG. 3). As shown in FIG. 5, the magnet arrangement has an annular recess 13a provided in a middle portion of the outer periphery thereof (i.e., a middle portion of the outer periphery of the magnet unit 3) as extending circumferentially thereof. That is, the permanent magnets 15a, 15b each have a recess 16 provided in a middle portion of the outer periphery thereof as extending across the middle portion of the outer periphery. With the permanent magnets combined into the magnet unit 13, the annular recess 13a is constituted by the recesses 16. The annular recess 13a prevents the spiral coils 14 (wound around the annular recess 13a and accommodated in the annular recess) (see FIG. 7) from being damaged in friction contact with the interior surface of the tube body 11 when the EMAT 1 is inserted into the tube body 11 as will be described later. The depth of the annular recess is determined according to the diameter of a wire material for the spiral coils 14, and the width of the annular recess is determined according to the width of the wound spiral coils 14.

Figure 6:
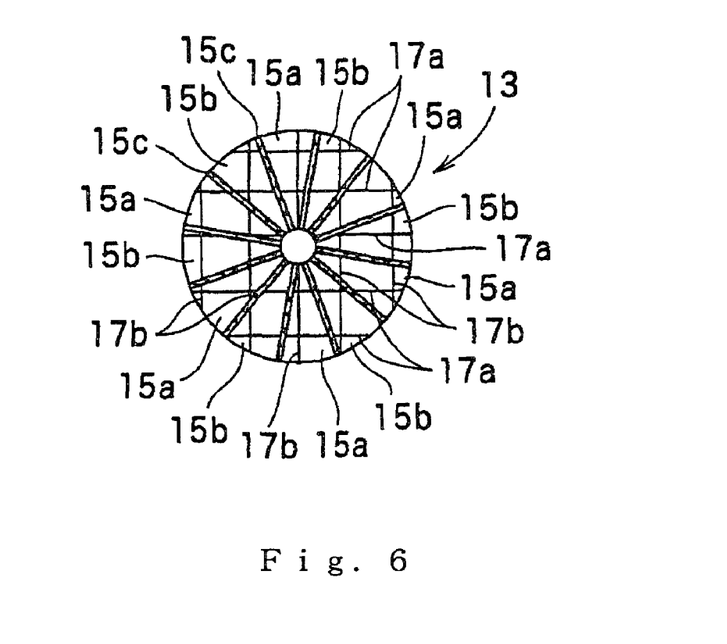
FIG. 6 is a diagram of an end face of the magnet unit.

In each of opposite end faces of the magnet arrangement (i.e., in each of axially opposite end faces of the magnet unit 13), as shown in FIG. 6, a plurality of recessed groove-like slits 17a (five slits in this embodiment, but the number of the slits may be one or any number) formed by cutting are arranged at predetermined intervals (equidistantly or non-equidistantly) as extending parallel to each other through the end face, and a plurality of recessed groove-like slits 17b (five slits in this embodiment, but the number of the slits may be one or any number) formed by cutting are arranged at predetermined intervals (equidistantly or non-equidistantly) as extending parallel to each other and perpendicularly to the slits 17a. The slits 17a, 17b (not shown in FIGS. 3 and 4) are effective in improving the S/N ratio (signal-to-noise ratio), thereby reducing the noise. The slits 17a, 17b each have a width of 0.2 to 0.4 mm and a depth of 1.0 to 1.5 mm.

The spiral coils 14 (see FIG. 3) are wound around the annular recess 13a for generating eddy currents in the fin-implanted heat transfer tube 2 to generate an electromagnetic force substantially parallel to the interior surface of the tube body 11. As described above, the spiral coils 14 include the transmission spiral coil 14a and the reception spiral coil 14b, which are alternately arranged axially of the magnet arrangement (i.e., axially of the magnet unit 13) (see FIG. 7). The coils 14a, 14b are each connected to the amplifier provided in the detector 5 (see FIG. 1) at one end thereof, and the other ends of the coils 14a, 14b are connected to the ground. In FIG. 5, a reference numeral 18 denotes a coil routing slit provided in the outer periphery of the magnet unit 13 as extending axially of the magnet unit for smoothly routing end portions (four end portions) of the spiral coils 14 for connection. Thus, the lead portions of the spiral coils are prevented from overlapping with the other portions of the spiral coils 14 wound around the annular recess 13a.

When a high frequency electric current flows through the transmission spiral coil 14a, shear waves or axially symmetric SH waves 3 polarized on the interior surface of the tube body 11 as having nodes circumferentially equiangularly distributed at predetermined positions on the interior surface are excited in the interior surface of the tube body 11. The axially symmetric SH waves 3 are generated on the interior surface of the tube body 11. An SH wave generating direction is circumferential on the interior surface of the tube body 11, and an SH wave amplitude direction is parallel to the interior surface of the tube body 11 and axial of the tube body 11. The excited axially symmetric SH waves 3 induce electric current in the reception spiral coil 14b, and the voltage of the electric current is detected to determine an acoustic pressure.

The computer 6 applies an operation signal to the burst wave generator provided in the detector 5 for operating the EMAT 1, then amplifies burst waves generated by the burst wave generator, and supplies the burst waves to the transmission spiral coil 14a to excite the axially symmetric SH waves 3 in the interior surface of the tube body 11 of the fin-implanted heat transfer tube 2. The burst wave generator sequentially generates signals of different frequencies at predetermined time intervals. The excited axially symmetric SH waves 3 are propagated circumferentially on the interior surface of the tube body 11 to cause resonance. The axially symmetric SH waves 3 causing the resonance at a frequency are detected by the reception spiral coil 14b, and detection signals are applied to a signal analyzer of the computer 6 through the amplifier and the A/D converter.

The signal analyzer includes means which determines the amplitudes of the detection signals inputted from the A/D converter, i.e., the acoustic pressure levels of the axially symmetric SH waves 3, then detects a resonant frequency which is defined as a frequency at a maximum acoustic pressure level in an acoustic pressure distribution obtained as a function of frequency through the excitation/reception/acoustic pressure determination process, and detects reduction in wall thickness due to corrosion or determines a residual wall thickness based on the detected resonant frequency. The signal analyzer receives the frequency of the driving signal and a reception signal applied from the A/D converter, and records the frequency and the reception signal in a correlated manner. The signal analyzer determines the frequency at the maximum acoustic pressure as the resonant frequency on the basis of the record.

The signal analyzer includes an LUT (lookup table) which indicates a relationship between the resonant frequency and the wall thickness. With reference to the LUT, the wall thickness is determined based on the previously determined resonant frequency. The resonant frequency of a tube body 11 having a reduced wall thickness due to corrosion of an interior surface thereof is different from the resonant frequency of a normal tube body 11 determined in a manner to be described later. Therefore, if a resonant frequency different from the resonant frequency of the normal tube body 11 is detected, the corrosion is detected based on the LUT.

On the other hand, a tube body 11 artificially formed with a plurality of reduced wall thickness portions having different depths is prepared, and resonant frequencies are determined for the respective reduced wall thickness portions with the use of the EMAT 1. Thus, a multiplicity of experiment data are collected to prepare a table or a mathematical formula (in this embodiment, the mathematical formula) which indicates a relationship between the residual wall thickness (or hole depth) of the reduced wall thickness portion and the resonant frequency. This permits evaluation of a flaw size (in this embodiment, the residual wall thickness of the reduced wall thickness portion). Further, the resonant frequency of the normal tube body 11 is determined with the use of the EMAT 1, and experiment data for the normal tube body 11 are collected. These experiment data show that there is a certain relationship, for example, between the residual wall thickness (or hole depth) and the resonant frequency and, as the residual wall thickness is reduced (i.e., the hole depth of the reduced wall thickness portion is increased), the resonant frequency is increased. This makes it possible to determine the flaw size on the basis of the experiment data, or to detect a certain problem occurring on the interior surface of the tube body 11 on the basis of a change in resonant frequency.

The feeder 7 is controlled by the computer 6 and, when occurrence of corrosion is detected on the basis of the result of inspection scanning, the inspection accuracy is increased for more precise flaw detection by reducing the feed amount of the feeder 7 for reduction of an inspection pitch. Further, the detection position of the EMAT 1 (a distance from a tube end of the tube body 11) is automatically inputted to the computer 6 from a scanning distance detector (not shown) incorporated in the feeder 7, and reflected on the data analysis.

Figure 8:
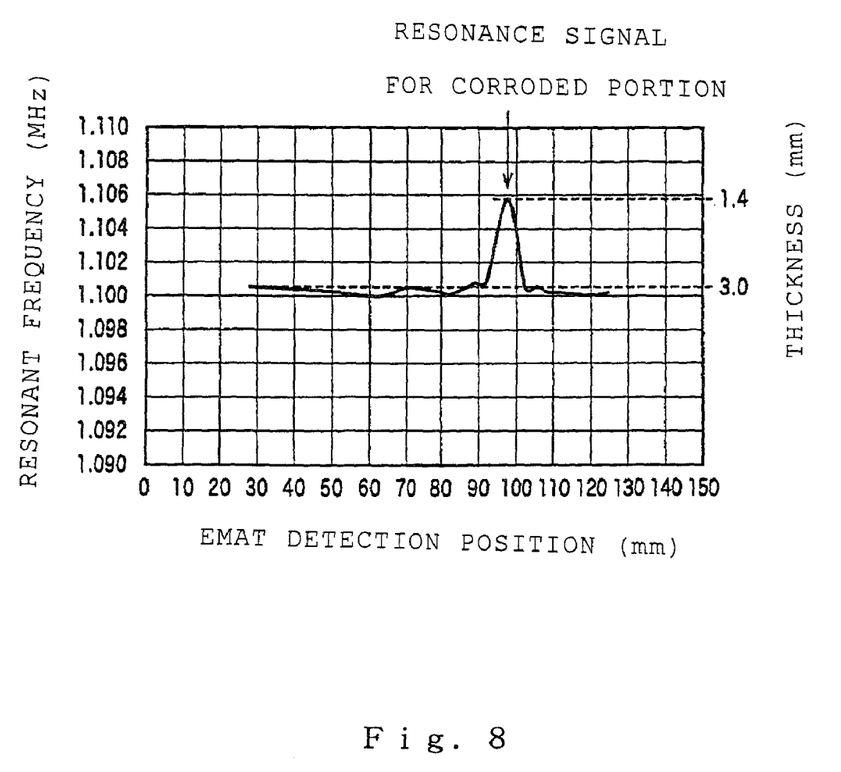
FIG. 8 is a diagram for explaining a graph to be displayed on a display screen.

The output device 8 has display means (not shown) and a graph (see FIG. 8) with the detection position (mm) of the EMAT 1 plotted as abscissa and the resonant frequency (MHz) at the detection position plotted as ordinate is displayed on a display screen of the display means. With reference to the resonant frequency and the amplitude (i.e., a change in resonant frequency) displayed on the display screen, a resonance signal indicating the occurrence of corrosion on the interior surface of the tube body 11 and the position of the corrosion (the distance from the tube end of the tube body 11) are detected. Where a list indicating the relationship between the resonant frequency and the wall thickness of the tube body 11 is displayed on a lateral side of the graph, or where a list indicating the relationship between the resonant frequency and the wall thickness of the tube body 11 is prepared based on the experiment data, the wall thickness (flaw size) of the corroded portion of the tube body 11 can be determined based on the resonance signal with reference to the list.

With the use of the electromagnetic ultrasonic flaw detection apparatus described above, the corrosion of the interior surface of the tube body 11 can be detected, for example, in the following manner. That is, the feeder 7 is first actuated to insert the EMAT 1 into the tube body 11 and move the EMAT 1 axially along the entire length of the tube body 11. During the movement, the interior surface of the tube body 11 is inspected by utilizing the axially symmetric SH waves 3 generated by an electromagnetic force by the EMAT 1, and the resulting inspection data is inputted to the computer 6. Further, the movement distance of the EMAT 1 (the distance from the tube end of the tube body 11) is detected by the scanning distance detector during the movement, and the resulting detection data is inputted to the computer 6. Based on the data and the graph displayed on the display screen of the output device 8, the presence of a corroded portion is checked and the size of the corroded portion is detected. Further, an inspection record taken along the entire length of the tube body 11 is prepared by printing the inspection data as an X-Y chart on a recording sheet by the output device 8. In a graph shown in FIG. 8, for example, a normal portion of the tube body 11 has a wall thickness of 3.0 mm, but a portion of the tube body 11 for which the resonance signal is generated has a wall thickness of 1.4 mm.

In this embodiment, as described above, the corrosion of the interior surface of the tube body 11 of the fin-implanted heat exchange tube 2 can be highly accurately detected. In addition, the use of the EMAT 1 makes it possible to achieve the flaw detection in a shorter period of time than the conventional ultrasonic flaw detection method, thereby permitting 100% inspection within a process at reduced costs. Further, the EMAT 1 does not require a contact medium such as water, obviating the need for the post treatment (dehydration or the like) of the tube body 11. In addition, the inspection for the flaw detection can be performed on any fin-implanted heat transfer tube 2 irrespective of the type of a fluid passing through the heat transfer tube. Since the EMAT 1 is adapted for non-contact inspection, the tube body 11 can be inspected for corrosion even with scale deposited on the interior surface thereof. Therefore, time and costs required for a pretreatment can be reduced.

Figure 9:
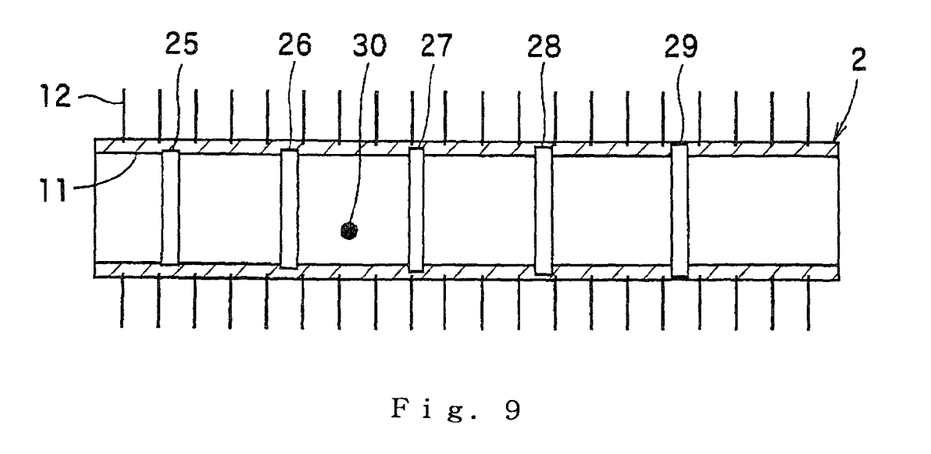
FIG. 9 is a diagram for explaining a test piece.
Figure 10:
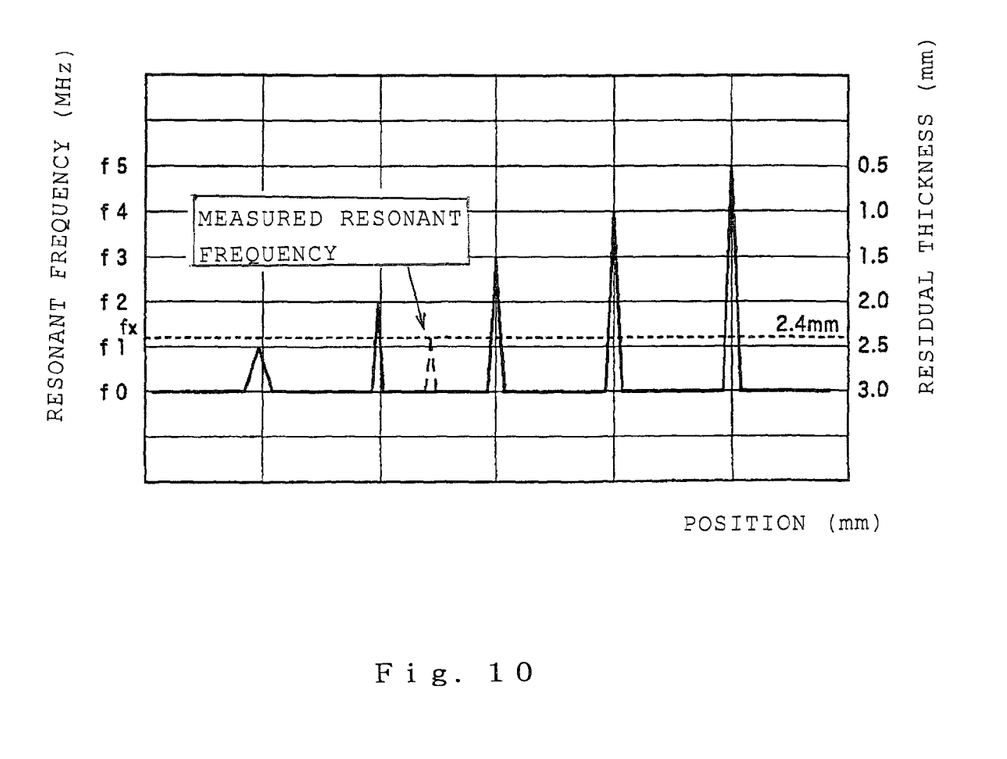
FIG. 10 is a diagram for explaining a graph to be displayed on the display screen.

For the collection of the multiplicity of data in the embodiment described above, a plurality of reduced wall thickness portions 25 to 29 having different depths, for example, are provided in an interior surface of a tube body 11 (test piece) as shown in FIG. 9, and resonant frequencies f1 to f5 (MHz) for the respective reduced wall thickness portions 25 to 29 are measured with the use of the EMAT 1. For the reduced wall thickness portions 25 to 29 having corrosion amounts and residual thicknesses (residual wall thicknesses) set as shown in Table 1, a measurement result as shown in FIG. 10 was obtained. These data show that there is a certain relationship between the resonant frequency and the corrosion amount or the residual thickness and, as the residual thickness is reduced (i.e., the hole depth of the reduced wall thickness portion is increased with an increased corrosion amount), the resonant frequency is increased. This makes it possible to determine the flaw size on the basis of the data, or to detect a certain problem occurring on the interior surface of the tube body 11 on the basis of a change in resonant frequency. Where a portion indicated by a black point 30 in FIG. 9 is corroded, for example, the residual thickness and position of the corroded portion are determined (in this example, the residual thickness is 2.4 mm and the corrosion amount is 0.6 mm) by measuring a resonant frequency fx for the corroded portion.

TABLE 1

|  | Reduced wall thickness portion | | | | | |
|---|---|---|---|---|---|---|
|  |  | 25 | 26 | 27 | 28 | 29 |
| Corrosion amount (mm) | 0 | 0.5 | 1.0 | 1.5 | 2.0 | 2.5 |
| Residual thickness (mm) | 3.0 | 2.5 | 2.0 | 1.5 | 1.0 | 0.5 |
| Resonant frequency (MHz) | f0 | f1 | f2 | f3 | f4 | f5 |

Note 1:
A portion having a corrosion amount of 0 mm and a residual thickness of 3.0 mm is formed with no reduced wall thickness portion.
Note 2:
See FIG. 10 for resonant frequencies.

Figure 11:
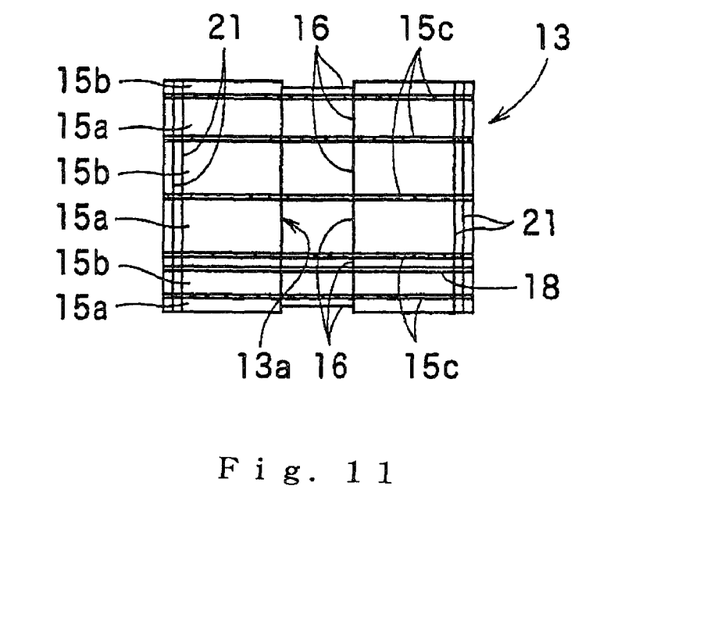
FIG. 11 is a side view illustrating a modification of the EMAT.

FIG. 11 illustrates a modification of the EMAT 1. In the modification, the permanent magnet unit 13 has slits 17a, 17b (see FIG. 6) formed in axially opposite end faces thereof by cutting as well as a plurality of annular recessed groove-like slits 21 (two slits in this embodiment, but the number of the slits may be one or any number) formed in axially opposite end portions of the outer periphery of the permanent magnet unit 13 as extending circumferentially. Except for the aforementioned arrangement, the modification has substantially the same construction as the EMAT 1 of the embodiment described above. Therefore, like components are denoted by like reference characters. The use of the EMAT 1 of the modification ensures the same function and effect as the embodiment described above. In addition, the provision of the plurality of annular slits 21 in the axially opposite edge portions of the outer periphery of the permanent magnet unit 13 further improves the S/N ratio, thereby reducing the noise.

EXAMPLE 1 AND 2, AND COMPARATIVE EXAMPLE 1

Figure 12:
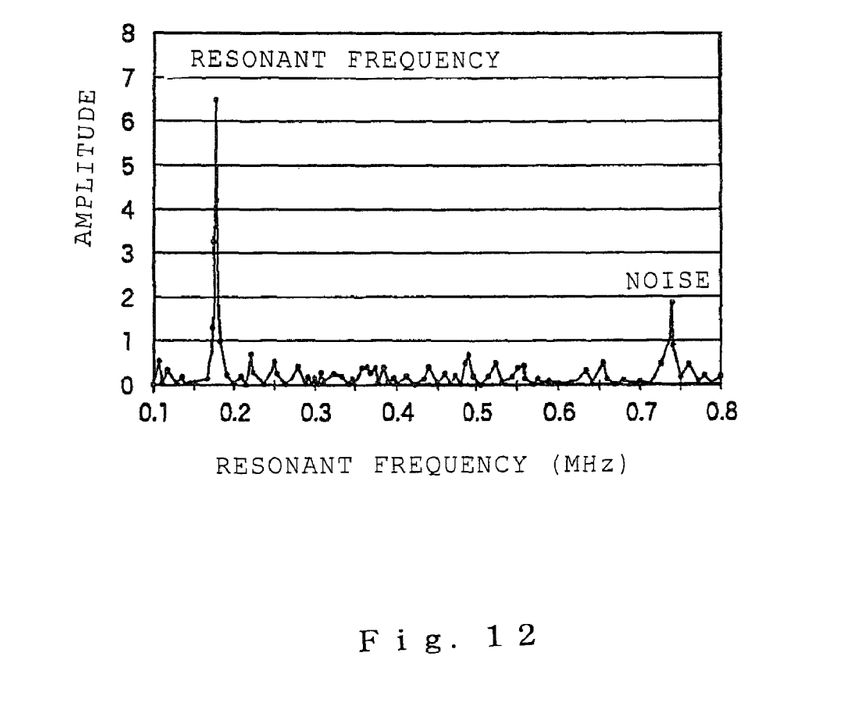
FIG. 12 is a diagram showing a measurement result.
Figure 13:
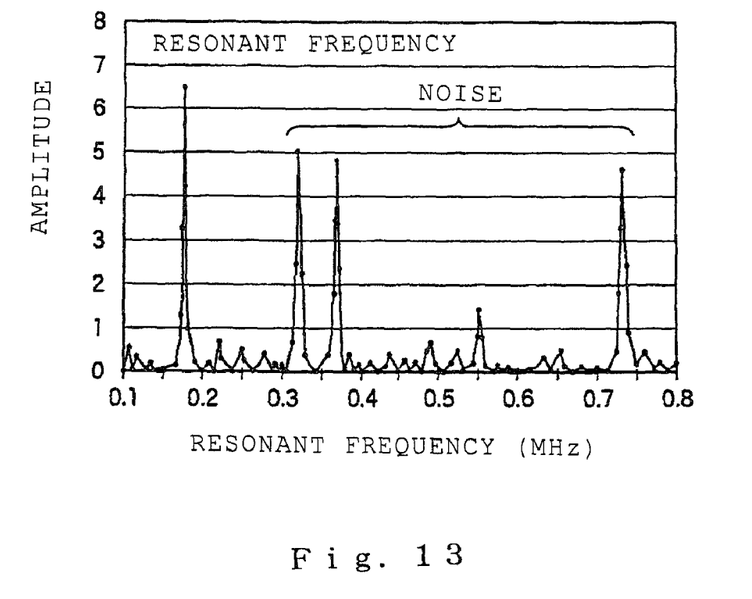
FIG. 13 is a diagram showing another measurement result.
Figure 14:
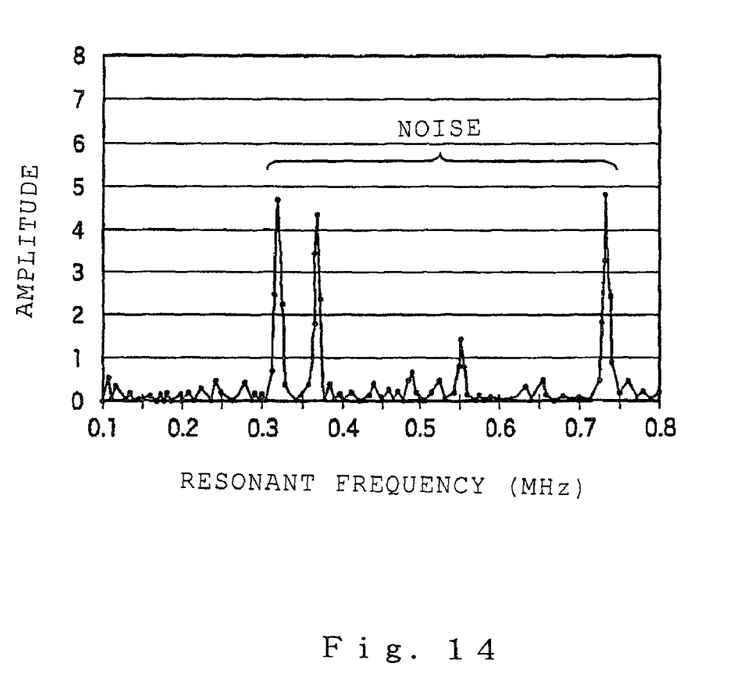
FIG. 14 is a diagram showing further another measurement result.

A fin-implanted heat transfer tube 2 and a heat transfer tube (not shown) with L-shaped wound fins were prepared which each had a corroded portion in an interior surface thereof. An EMAT 1 according to the embodiment described above and an EMAT 1' having substantially the same construction as the EMAT 1 except that no slits 17*a*, 17*b* were provided in axially opposite end faces of the magnet arrangement were prepared. A resonant frequency was measured in a portion of the fin-implanted heat transfer tube 2 around the corroded portion by the EMAT 1 (Example 1), and a resonant frequency was measured in the portion of the fin-implanted heat transfer tube 2 around the corroded portion by the EMAT 1' (Example 2). A resonant frequency was measured in a portion of the heat transfer tube with the L-shaped wound fins around the corroded portion by the EMAT 1' (Comparative Example 1) Measurement results are shown in FIG. 12 (Example 1), FIG. 13 (Example 2) and FIG. 14 (Comparative Example 1). These measurement results show that: the resonant frequency was not detected in the corroded portion and a noise level was high in Comparative Example 1; the resonant frequency was detected and a noise level was high in Example 2; and the resonant frequency was detected and a noise level was very low in Example 1.

In the embodiment described above, the EMAT 1 has a generally hollow cylindrical shape. However, the shape of the EMAT 1 is not limited to the hollow cylindrical shape, but may be a solid cylindrical shape. In the embodiment described above, the fin-implanted heat transfer tube 2 includes the carbon steel tube body 11 and the nonferrous metal heat transfer fins 12 such as of aluminum, but any of various fin-implanted heat transfer tubes 2 may be employed. In the embodiment described above, the fin-implanted heat transfer tube 2 is a straight tube, but may be a curved tube having any of various shapes including a U-shape.

In the embodiment described above, the magnet unit 13 is segmented into 12 parts (or includes 12 permanent magnets 15*a*, 15*b*), but this is not limitative as long as the number of the parts of the segmented magnet unit is plural. For the detection of the corrosion of the interior surface of the fin-implanted heat transfer tube 2, the magnet unit may be segmented into 10, 12 or 14 parts. However, division of the magnet unit into 16 or greater parts is not suitable for the detection of the corrosion of the interior surface of the fin-implanted heat transfer tube 2. The resonant order (the first order mode to the Nth order mode) employed for the detection of the corrosion of the interior surface is optimally the first order mode, and preferably up to the third order mode.

What is claimed is:

1. An electromagnetic ultrasonic flaw detection method comprising:
    moving an electromagnetic ultrasonic transducer in a fin-implanted heat transfer tube of an air cooling heat exchanger axially of the tube;
    causing the electromagnetic ultrasonic transducer to generate an axially symmetric SH wave by utilizing an electromagnetic force to vibrate a tube body of the fin-implanted heat transfer tube to cause resonance;
    causing the electromagnetic ultrasonic transducer to detect a resonant frequency; and
    if the detected resonant frequency is different from a resonant frequency observed when the tube body has a normal wall thickness, judging that an interior surface of the tube body has a corroded portion,
    wherein the electromagnetic ultrasonic transducer includes a permanent magnet unit having a hollow or solid cylindrical shape, and a transmission coil and a reception coil which are wound around the permanent magnet unit, and
    wherein the permanent magnet unit includes a plurality of permanent magnets each having opposite poles respectively disposed at a greater radius portion and a smaller radius portion thereof and arranged circularly with their polarities alternately reversed circumferentially of the permanent magnet unit.

2. The electromagnetic ultrasonic flaw detection method according to claim 1, wherein the tube body of the fin-implanted heat transfer tube is composed of a carbon steel, and fins of the heat transfer tube are composed of a nonferrous material.

3. The electromagnetic ultrasonic flaw detection method according to claim 1, wherein the tube body of the fin-implanted heat transfer tube is composed of a carbon steel, and fins of the heat transfer tube are composed of aluminum.

4. The electromagnetic ultrasonic flaw detection method according to claim 1, wherein a resonant order of the axially symmetric SH wave is a first order mode.

5. The electromagnetic ultrasonic flaw detection method according to claim 2, wherein a resonant order of the axially symmetric SH wave is a first order mode.

6. The electromagnetic ultrasonic flaw detection method according to claim 3, wherein a resonant order of the axially symmetric SH wave is a first order mode.

7. An electromagnetic ultrasonic transducer comprising:
    a permanent magnet unit having a hollow or solid cylindrical shape; and a transmission coil and a reception coil which are wound around the permanent magnet unit;
    wherein the permanent magnet unit includes a plurality of permanent magnets each having opposite poles respectively disposed at a greater radius portion and a smaller radius portion thereof, and arranged circularly with their polarities alternately reversed circumferentially of the permanent magnet unit;
    wherein the permanent magnet unit has opposite end faces each formed with a plurality of slits intersecting each other.

8. An electromagnetic ultrasonic flaw detection method comprising:
    moving an electromagnetic ultrasonic transducer in a fin-implanted heat transfer tube of an air cooling heat exchanger axially of the tube;
    causing the electromagnetic ultrasonic transducer to generate an axially symmetric SH wave by utilizing an electromagnetic force to vibrate a tube body of the fin-implanted heat transfer tube to cause resonance;
    causing the electromagnetic ultrasonic transducer to detect a resonant frequency; and
    if the detected resonant frequency is different from a resonant frequency observed when the tube body has a normal wall thickness, judging that an interior surface of the tube body has a corroded portion,
    wherein the electromagnetic ultrasonic transducer includes a permanent magnet unit having a hollow or solid cylindrical shape, and a transmission coil and a reception coil which are wound around the permanent magnet unit.

* * * * *